(12) United States Patent
Miller et al.

(10) Patent No.: US 8,688,262 B1
(45) Date of Patent: Apr. 1, 2014

(54) SEMI-AUTOMATED LAB TUBE SELECTION APPARATUS FOR RACK CONTAINED TUBES

(76) Inventors: David B. Miller, Orinda, CA (US);
Alexander V. Drynkin, San Ramon, CA (US)

( * ) Notice: Subject to any disclaimer, the term of this patent is extended or adjusted under 35 U.S.C. 154(b) by 562 days.

(21) Appl. No.: 12/927,059

(22) Filed: Nov. 4, 2010

(51) Int. Cl.
*G06F 7/00* (2006.01)

(52) U.S. Cl.
USPC .......... 700/215; 414/404; 294/103.1; 422/400

(58) Field of Classification Search
USPC ........................................................ 700/215
See application file for complete search history.

(56) References Cited

U.S. PATENT DOCUMENTS

| | | | |
|---|---|---|---|
| 7,494,168 B1 * | 2/2009 | Miller ........................ | 294/103.1 |
| 2005/0169733 A1 * | 8/2005 | Drynkin et al. ............... | 414/404 |
| 2010/0028214 A1 * | 2/2010 | Howard et al. ............... | 422/102 |
| 2012/0283867 A1 * | 11/2012 | Gelbman et al. .............. | 700/215 |

* cited by examiner

*Primary Examiner* — Gene Crawford
*Assistant Examiner* — Kyle Logan
(74) *Attorney, Agent, or Firm* — Richard Esty Peterson

(57) ABSTRACT

A tube handling system with a semi-automatic lab tube selection apparatus for enabling a user to pick a select lab tube in a standard lab tube holding rack with open-bottom wells that contain one or more lab tubes that includes a tube selection unit having, a housing with a top deck having a tube rack support, a transport mechanism contained within the housing having a carriage assembly, with the carriage assembly having a carrier with a push-pin, a drive system that moves the carrier and the push-pin under the tube rack support, and an actuator that raises the push-pin on command for removal, and, a control system to locate the carrier and the push-pin at a select location corresponding to a selected position under an open-bottom well of a tube rack positioned on the tube rack support to raise the push-pin for removal.

14 Claims, 5 Drawing Sheets

SEMI-AUTOMATED LAB TUBE SELECTION APPARATUS FOR RACK CONTAINED TUBES

BACKGROUND OF THE INVENTION

Field of the Invention

This invention relates to a semi-automated lab tube selection system for facilitating the removal of select lab tubes from a standard lab tube holding rack.

The semi-automated lab tube selection apparatus for rack contained tubes is a tube management system that assists a user such as a lab worker in identifying and selecting individual tubes that are contained in one or more tube racks and enabling the manual removal of the selected tube by an electro-mechanical push assembly. The electro-mechanical push assembly locates a push-pin under the selected tube and pushes the tube upwardly for convenient retrieval of the selected tube by the lab worker. In the preferred embodiment the semi-automated tube selection apparatus includes a visual display system and an associated processor and computer program to visually guide the lab worker in a pre-programmed procedure. In a preferred embodiment, the semi-automated tube selection apparatus is combined with a code scanner that reads a bar code on the bottom of tubes in the rack to identify individual tubes and correlate the tube identification with the tube location in the rack.

The semi-automated lab tube selection apparatus of this invention is designed to operate with the type of sample or test tube container as described in U.S. Pat. No. 6,663,836 of Kalmakis et al, issued Dec. 16, 2003. In the system described, tubes are retained in wells in a carrier rack in a uniform arrangement such as an orthogonal matrix having addressable locations. In one embodiment, the bottoms of the tubes are marked with an alphanumeric designation. The wells have open bottoms to expose the bottom of the tube for marking and for subsequent visual identification of the alphanumeric code. With the advent of bar code systems, particularly two-dimensional systems, such as the Data Matrix code system, detailed identity data can be imprinted in the small area available on the bottom of a small diameter tube. This type of tube rack carrier system lends itself to a multiplicity of automated tube selection opportunities incorporating the basic features of the subject invention.

For example, the semi-automated lab tube selection apparatus can comprise a simple keypad entry system to identify the location of the tube to be raised for manual retrieval with a simple controller sensing the numeric or alphanumeric input and directing the electro-mechanical assembly to locate the push-pin under the rack at the identified location of the target well. When located the apparatus will automatically raise the pin pushing a tube present in the well at the designated location upwardly for convenient gripping and removal by the user's fingers. This assist is particularly useful when small tubes are densely packed in a conventional tube rack.

With the addition of a display screen and a programmable processor, a variety of procedures can be established for tube management using pick and place protocols. Finally, when combined with a tube reader to identify selected tubes by their individual tube identification, then a complete tube management system can be devised according to the procedures desired by the operator. The tube reader is preferably a scanner that is combined as an accessory in one embodiment and as an integral part of the semi-automated lab tube selection apparatus in another embodiment. In the integrated embodiment, the complete system including the display can be incorporated into a desktop unit for plug and play convenience. In the modular embodiment, the display and programmable processor can comprise a general-purpose personal computer or a simple notebook portable that electronically connect the internal controller of the semi-automatic tube selection apparatus with an electronically connected tube scanner, that is either part of the tube selection apparatus or a separate module.

SUMMARY OF THE INVENTION

The semi-automatic tube selection apparatus of this invention is a laboratory device to assist the laboratory worker or technician in managing tubes and vials that are typically contained in tube racks for convenient use and storage. The modern tube racks are of different sizes to accommodate different numbers and sizes of tubes. The various sizes are somewhat standardized allowing laboratory equipment to be designed with these standards in mind. It is to be understood, that while a popular ninety-six-tube rack is being utilized in the preferred embodiment of the tube selection apparatus of this specification for purposes of demonstration, the described features of the disclosed invention are applicable to other standard and custom racks and tubes with appropriate modification of the structure of the described apparatus and modification of the programming coordinating the operation.

The preferred embodiment adopts the middle ground combination of the semi-automated tube selection apparatus with an integral tube scanner for coordinated operation by an auxiliary general purpose computer programmed with an application program for the desired routines for a tube management system. It is to be understood that the combined unit includes an internal controller having a dedicated processor that is electronically connected to the computer by wire or wirelessly. The cost of a computer, such as a notebook computer, is sufficiently low that incorporating the computer into the unit is frequently not cost justified. However, if the semi-automated tube selector were incorporated into a more sophisticated fully automated tube handling system, then integration of the general purpose programmable computer into the unit would likely be justified for the convenience of a plug and play unit.

The semi-automated tube selection apparatus of the preferred embodiment includes a housing with a substantially flat top deck with a fixed number of recesses for placement of standard tube racks. The tube racks are of the type that have tube wells with open bottoms with a rim sufficient to retain the tube but with an open area sufficient to view a 2D code marking on the bottom of the tube when seated in the well. The recesses in the deck provide for fixed placement of the tube rack on the deck in order that the mechanism for lifting a select tube can be accurately positioned under the target tube. Similarly, a recess is provided for scanning the tubes in a rack by fixing the positioning of the rack so that the scanned image can be registered with the rack for deciphering the identity of individual tubes in the matrix according to the address of the well in which a particular tube is situated. Other retainer means may be utilized to position the racks, such as elevated rails that frame the rack to maintain its location for accurate registration of the scanner and push mechanism.

It is to be understood that the preferred embodiment described in the detailed description may be modified without departing from the scope of the invention, which is defined by the claims. Other features may be added and certain features that are not essential to the basic invention may be deleted for reasons of economy or when user options are desired to be limited or restricted.

DETAILED DESCRIPTION OF THE PREFERRED EMBODIMENTS

Figure 1:
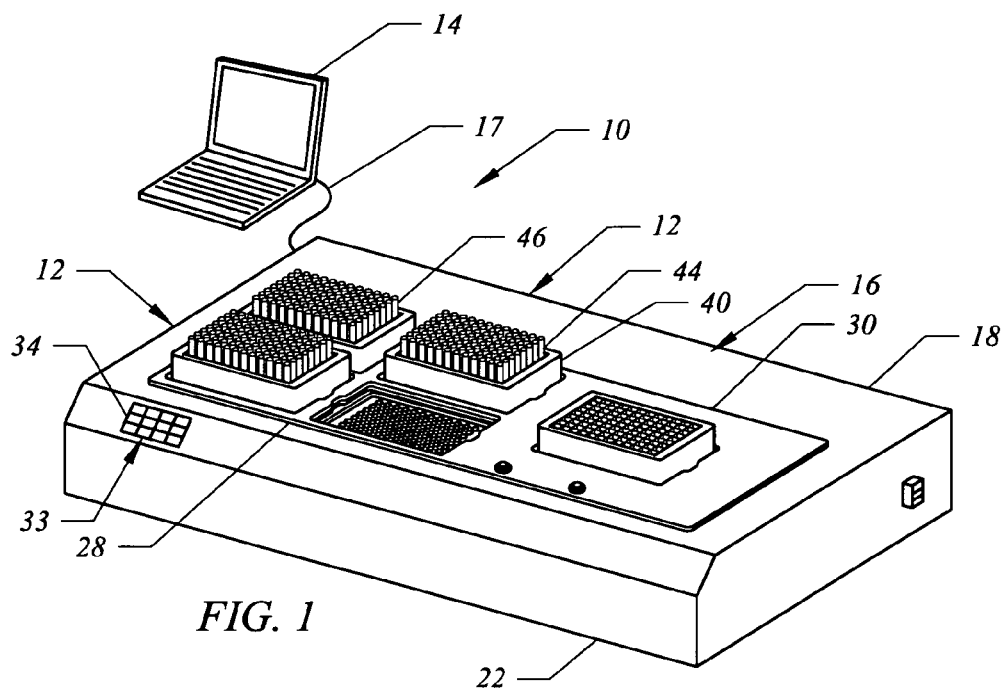
FIG. 1 is a perspective view of a semi-automatic lab tube handling system with a tube selection unit carrying tube racks and a connected programmable computer.

The semi-automatic lab tube selection apparatus of this invention is designated generally by the reference numeral 10 and set forth in FIG. 1 of the drawings as a counter-top tube handling system 12 that includes a programmable computer 14 as a system component.

The primary component of the tube handling system 12 is the semi-automatic tube selection unit 16. The tube selection unit 16 is preferably coupled to the programmable computer 14, which includes an application program that is preferably modifiable by the system operator to vary the protocol desired for a particular tube handling operation. The tube selection unit 16 has a housing 18 with a removable casing cover 20 that frames a top deck 22 and with a base 24 that supports the internal components. The tube selection unit 16 includes at least one internal controller 26 to control the electromechanical operations of the tube handling system 12 as shown in the perspective view of FIG. 2.

The preferred embodiment of the semi-automatic tube selector apparatus 10 combines a tube selector module 28 with a tube scanner module 30 in the single housing 18. The tube scanner module 30 preferably includes a separate controller 32 for serial or parallel control of the scanning operations. It is to be understood that the semi-automatic tube selection unit 16 can be a standalone unit with an input device such as a small touch-screen keypad 34 on the housing 18. It is recognized that for the rich environment of a programmable tube handling application, a computer 14, even a small notebook computer is preferred.

Figure 2:
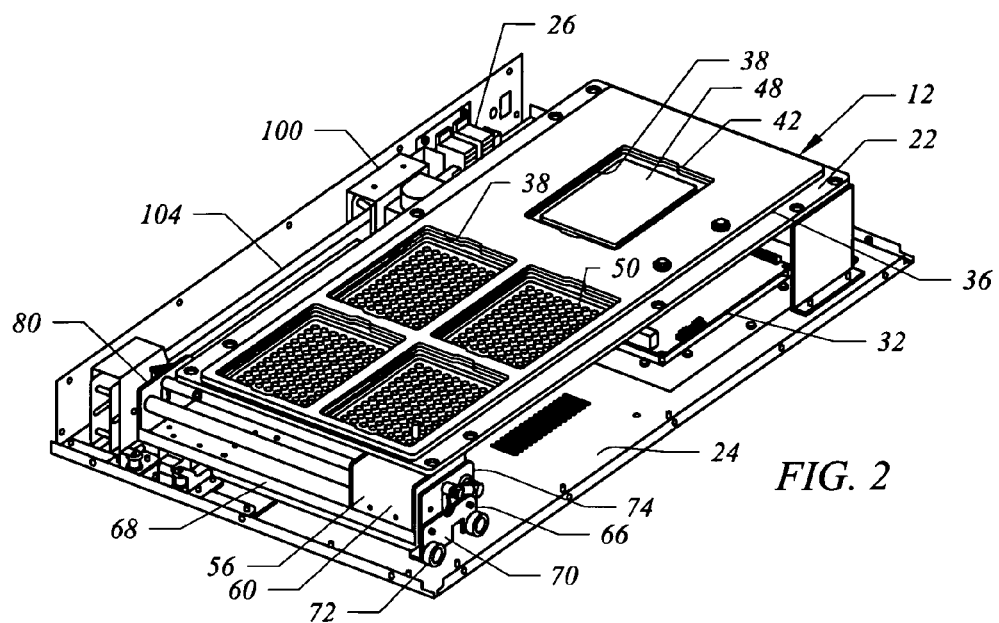
FIG. 2 is a perspective view of the tube selection unit of FIG. 1 with a casing cover removed to reveal internal components.

The housing 18 is generally a rectangular, box-like, low-profile, structure with the casing cover 20 providing a protective enclosure for the contained electromechanical components that perform the tube selection and scanning functions. The top deck 22 supports a platen 36 with rectangular stepped cutouts 38 as shown in FIG. 2 to support and position tube holding racks 40 as shown in FIG. 1. The cutouts 38 have opposed finger notches 42 to enable a user to easily remove a rack from the recess formed by the cutouts 38 that frame the rectangular racks 40.

As shown in FIG. 1, the racks 40 have wells 44 for receiving tubes 46 which are uniformly organized in standardized rows and columns of a matrix. The racks 40 are of a conventional type that have openings in the bottom of each well to enable markings on the bottom of the tubes to be visible. Typically, the markings are a type of 2D barcode that is machine-readable and is unique for each tube.

In the scanner module 30, the cutout 38 positions the rack 40 over a glass scanner plate 48, shown in FIG. 2 and as tubes are placed in the rack, the underlying scanner bar (not visible) scans the underside of the rack, and, with the software of the applications program identifies the tubes and their location in the rack 40. For one scheme of pick and place operations, the tube filled racks 40, as shown in the selector module 28 of the tube selection unit in FIG. 1, are first scanned in the scanner module 30 before being seated in an ordered manner in the cutouts 38 of the selector module 28.

In this manner, the tubes 46 in the racks 40 are first identified, such that the application program can identify which tube from which rack is to be picked and removed, or placed at which location in a receiving rack. The receiving rack is advantageously placed in the cutout 38 of the scanner module 30, to verify that a picked tube 46 is correctly placed in the proper well 44 in the receiving rack 40.

Figure 3:
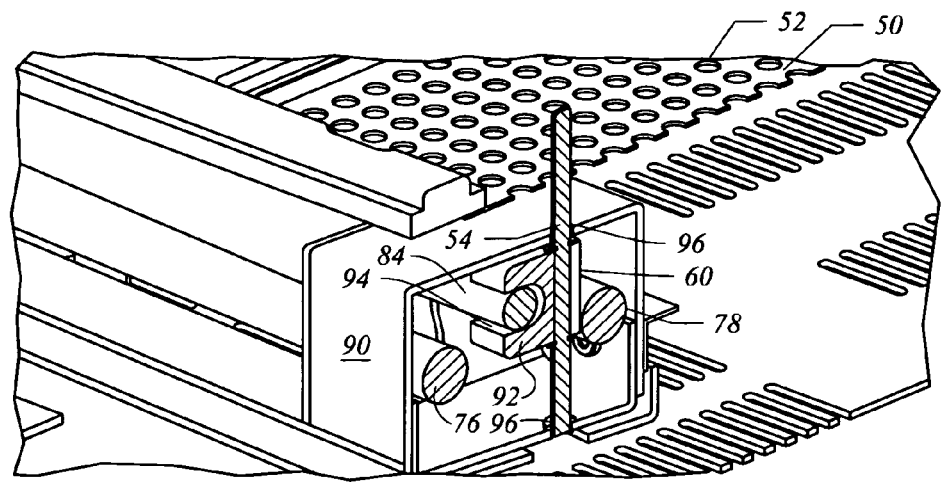
FIG. 3 is an enlarged broken-away view partially in cross section of the push-pin on the electromechanical carriage assembly of the tube selection unit of FIG. 2.

In the selector module 28, the cutouts 38 position the racks 40 over a screen 50 that is fastened to the underside of the platen 36 as shown in the enlarged fragmented cross-sectional view of FIG. 3. The screen 50 is a plate with a series of holes 52 arranged in four arrays that match the location of the bottoms of the wells 44 when a rack 40 is positioned in the recess of a cutout 38. In this manner a push-pin 54 that is inserted up through a particular hole 52 will contact the underside of a tube 46 in the corresponding well 44 and raise the tube 46 for easy visual identification and manual removal. The picked tube 46 can then be placed in the desired location in the receiving rack 40 and the placement verified by a scan.

Location and operation of the push-pin 54 is accomplished by an electromechanical carriage assembly 56. The carriage assembly has an X-Y random access drive system 58 to access any tube well in any order. The drive system 58 includes the controller 26 that executes commands from the input device 59, for example, the touch screen 34 or the programmed computer 14, and moves a push-pin carrier 60 to the desired location. In the preferred embodiment the input device 28 comprises the programmed computer 14 with an application program having a user interface 62, for example, as shown in part by the screen shot 64 of FIG. 6, to guide a user through a devised protocol.

The push-pin carrier 60 is shown in part in FIG. 2 seated on the near side of a support carriage 66 that spans the majority of the width of the base 24 of the housing 18. The support carriage 66 is an elongated tray-like structure 68 supported at its distal end 70 by a pair of bearing wheels 72.

Figure 4:
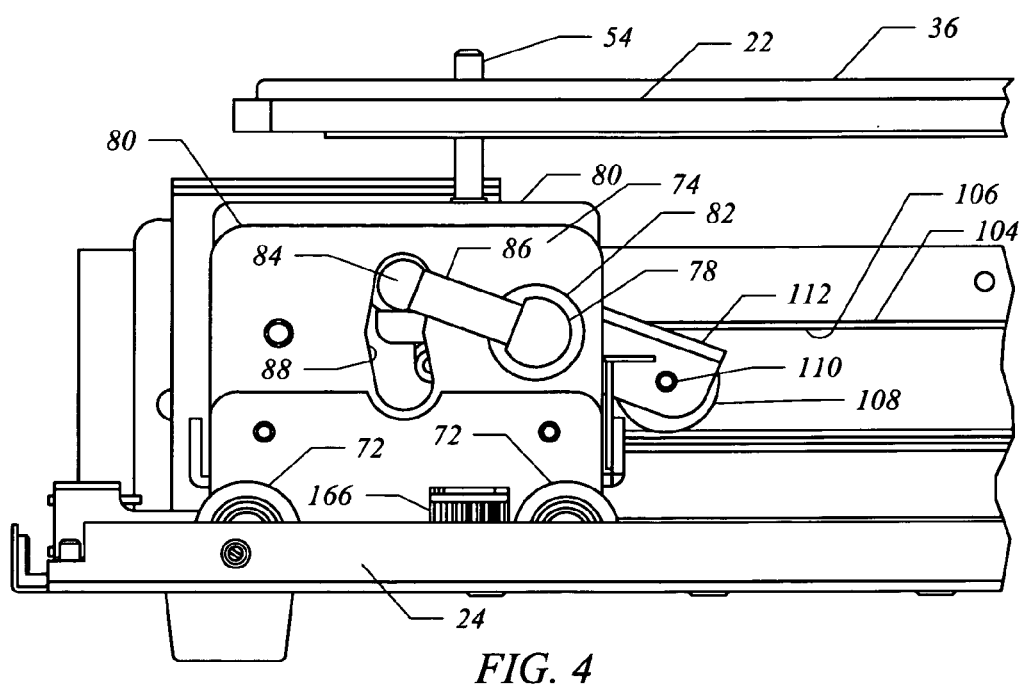
FIG. 4 is an enlarged broken-away side view of the push-pin apparatus of the electromechanical carriage assembly of FIG. 3.

The distal end 70 has an end plate 74 that supports the ends of two guide rods 76 and 78, which are shown in FIGS. 3 and 4. The push-pin carrier 60 rides on the two guide rods 76 and 78 when traversing the span of the support carriage 66 between distal end plate 74 and an opposite end plate 80. One of the guide rods 78 passes through the end plate 74 on a bearing 82 as shown in FIG. 4 and is rotatable. The rotatable guide rod 78 is connected to a smaller diameter actuator rod 84 by spaced strut pins 86 located next to the end plates 74 and 80 that span and interconnect the two rods 78 and 80.

The actuator rod 84 passes through an arcuate aperture 88 in the casing 90 of the push-pin carrier 60 and, as shown in the enlarged cross-sectional, perspective view of FIG. 4, engages a cam block 92 that is fixed to the push-pin 54. The cam block 92 has a side slot 94 in which the actuator rod 84 is seated that forms a cam surface to accommodate the arcuate travel of the actuator rod 84 when the rotatable guide rod 78 is rotated. The cam block 92 translates the arcuate displacement as linear motion to the attached push-pin 54 which is constrained by bearings 96 in the top and bottom of the casing 90. In this manner as the guide rod 78 is rotated or pivoted a fraction of a rotation the push-phi 54 is lifted as shown in FIGS. 3 and 4. When actuation ceases, the push-pin 54 drops until the cam block 92 rests on the inside bottom of the casing 90.

Actuation of the push-pin 54 at any position of the support carriage 66 in its travel back and forth across a part of the base 24 is accomplished by a shuttle assembly 100 located along part of the edge of the base 24 as shown in FIG. 2. The shuttle assembly 100 has a guide casement 102 that contains a shuttle 104. The shuttle 104 has a guide channel 106 for a tracking wheel 108 on an axle 110 on the end of an arm 112 that is fixed to the pivotal guide rod 78, as shown in FIG. 4. When the shuttle 104 is retracted, the guide channel rises and the tracking wheel 108 translates the elevated shuttle as a pivotal motion to the guide rod 78 and attached actuator rod 84. Pivot of the actuator rod 84 raises the push-pin 54.

Figure 5:
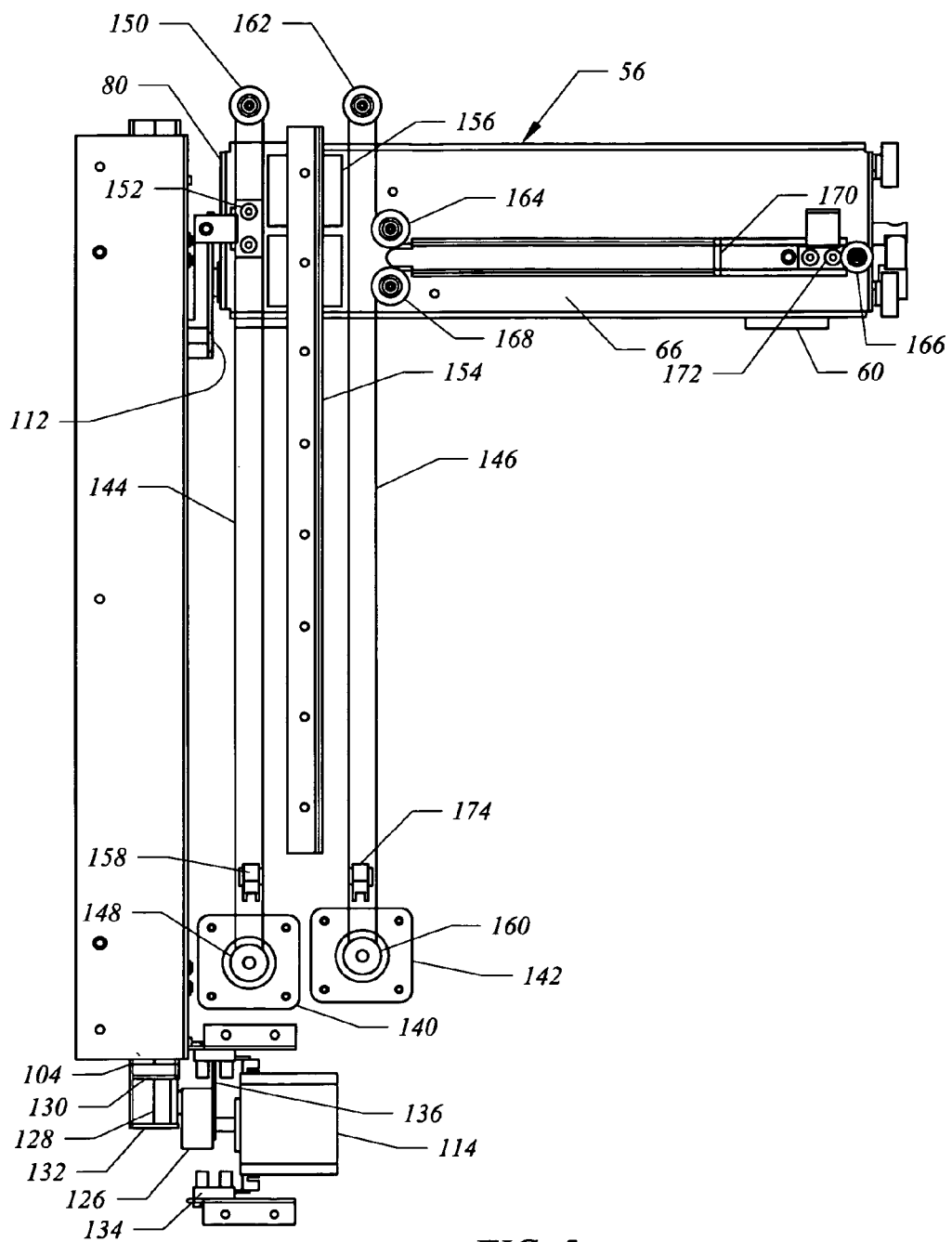
FIG. 5 is a plan view of the electromechanical carriage assembly of FIG. 2 removed from the other components of the tube selection unit.
Figure 7:
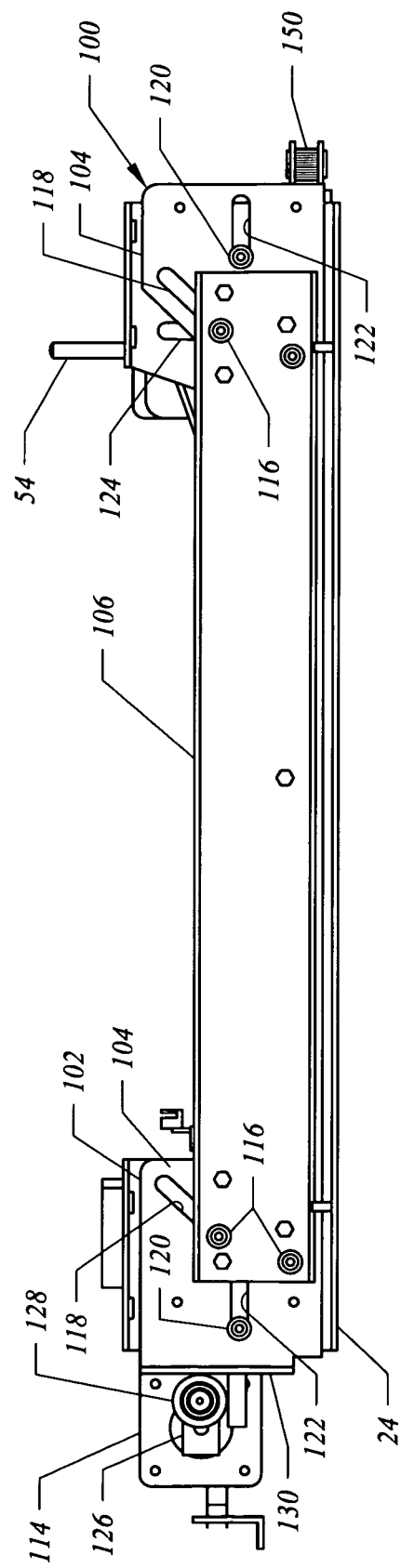
FIG. 7 is a side elevational view of the electromechanical carriage assembly of FIG. 5.

Raising the guide channel 106 by the shuttle 104 is accomplished by horizontal displacement of the shuttle 104 by an actuator motor 114 on the base 24 at one end of the shuttle 104, as shown in FIGS. 5 and 7. The guide channel 106 is suspended at each end by cross pins 116, which engage slots 118 in the raised ends of the shuttle 104. The slots 118 are sloped at about a forty-five degree angle such that the shuttle 104 when actuated by the motor displaces horizontally as restrained by the pins 120, which engage horizontal slots 122 in the guide casement 102. Horizontal displacement of the guide channel 106 is restrained by the cross pins 116 of the guide channel 106 which extend into vertical slots 124 in the guide casement 102.

The actuator motor 114 has a crankshaft 126 that has an off-center cam wheel 128 that engages parallel plates 130 and 132 at the end of the shuttle 104 such that a half turn displaces the shuttle 104 one direction or the other. Sensors 134 determine the position of the crankshaft 126 and hence the push-pin position by the location of a flag 136 on the crankshaft 126 as shown in the bottom view of FIG. 5 with the base 24 removed.

The actuator motor 114 is in a motor compartment 138 with a pair of bi-directional drive motors 140 and 142 in the drive system 58 for movement of the push-pin carrier 60 by a pair of fixed length drive belts 144 and 146. The belt path of each of the drive belts 144 and 146 is shown most clearly in FIG. 5.

Referring to FIG. 5, the support carriage 66 of the carriage assembly 56 is displaced by the drive belt 144 in a simple loop path around the drive motor drive capstan or wheel 148 and a distal idler wheel 150. The support carriage 66 is attached at one point on the drive belt 144 by a bracket 152. The support carriage 66 travels along a guide rail 154 by guide blocks 156. A sensor 158 tracks the movement of the drive belt 144 by counting traction grooves or markers on the inside of the belt 144. The sensor data allows the precise position of the support carriage 66 in its back and forth movement along the guide rail 154.

Fore and aft movement of the push-pin carrier 60 on the support carriage 66 is accomplished by a more complicated path of the drive belt 146. The drive belt loops around the capstan or drive wheel 160 of the drive motor 142, around a distal first idler wheel 162, around a second idler wheel 164 on the underside of the support carriage 66, around a third idler wheel 166 at the distal end of the underside of the support carriage 66 and around a fourth idler wheel 168 next to the second idler wheel 164 before returning to the drive wheel 160 of the drive motor 142.

The push-pin carrier 60 is connected at one point to the drive belt 146 through a slot 170 in the underside of the support carriage by a bracket 172. A sensor 174 tracks the movement of the drive belt 146, which is analyzed by a microprocessor in the internal controller 26. In the case of the positioning of the push-pin carrier 60 and hence the location of the push-pin 54, the analysis includes an adjustment for the displacement of the support carriage 66, which otherwise would cause a dislocation of the push-pin carrier 60. Essentially, the displacement of the drive belt 146 matches the displacement of the drive belt 144 simply to keep the push-pin carrier 60 in one place when the support carriage 66 is displaced. Movement of the push-pin carrier 60 is added to or subtracted from the movement of the support carriage 66 to obtain the desired fore or aft displacement of the push-pin carrier 60. It is to be understood that commands from the computer 14 are interpreted and executed by the internal controller as control signals to the drive motors 140 and 142 and actuator motor 114 for displacement and actuation of the push-pin 54 up through the screen 50.

Figure 6:
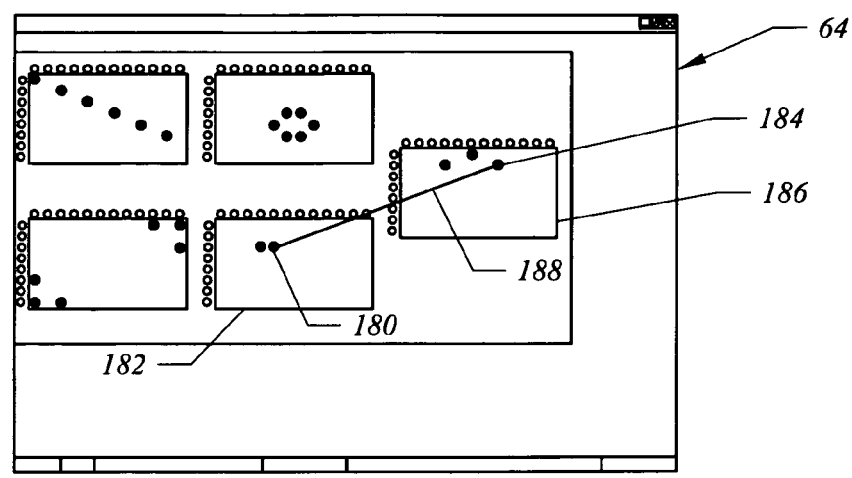
FIG. 6 is a typical screen display of the accessory computer or input device of the tube selection unit.

The screen shot 64 of FIG. 6 is illustrative of a visual sequence for moving designated tubes, for example, virtual tube 180 from a designated virtual tube rack 182 in the representation of the tube selector module to a designated virtual tube well 184 in the virtual tube rack 186 in the scanner module. The path line 188 illustrates the location of the actual tube that is to be automatically lifted by the push-pin 54 and retrieved by the user for placement into the actual well in accordance with the programmed protocol. The receiving rack on the scanner module can be easily scanned during the procedure to check that the instructed placement has been successfully accomplished.

These and other procedures and features of the lab tube selection apparatus 10 described in the preferred embodiment of this specification can be changed within the limits of the claims without departing from the scope of the invention to which applicant is entitled.

The invention claimed is:

1. A tube handling system with a semi-automatic lab tube selection apparatus for enabling a user to pick a select lab tube in a standard lab tube holding rack with open-bottom wells that contain one or more lab tubes comprising:
    a tube selection unit having,
        a housing with a top deck having a tube rack support platen with at least one stepped cutout that supports and positions the tube holding rack on the top deck,
        a transport mechanism contained within the housing having a carriage assembly, wherein the carriage assembly has a carrier with a push-pin, a drive system that moves the carrier and the push-pin under the tube rack support platen, and an actuator that raises the push-pin on command, and,
        a control system having electronic control components that operate the drive system to locate the carrier and the push-pin at a select location corresponding to a selected position under an open-bottom well of a tube holding rack positioned on the tube rack support platen, and that actuate the actuator to raise the push-pin, wherein a selected tube in the well of the tube holding rack at the selected position of the push-pin is raised for removal.

2. The tube handling system of claim 1 further comprising a tube scanner module, the tube scanner module being electronically connected to the control system wherein the tube scanner module has a glass scanner plate over which a tube holding rack with open-bottom wells is seated, wherein lab tubes having identification markings contained in the open-bottom wells are scanned under control of the control system for identification of the lab tubes in the tube holding rack.

3. The tube handling system of claim 2 wherein the tube scanner module is located in the same housing and the top deck is constructed to support both a tube holding rack of the tube selection unit and a tube holding rack of the tube scanner module.

4. The tube handling system of claim 3 wherein the top deck is constructed to support a plurality of tube holding racks in addition to a tube holding rack of the tube scanner module.

5. The tube handling system of claim 1 wherein the electronic control components that operate the drive system are located in a control compartment of the housing under the top deck.

6. The tube handling system of claim 5 wherein the push-pin is connected to a mechanical actuator that is operated by an electronic control component in the control compartment of the housing.

7. The tube handling system of claim 6 wherein the mechanical actuator includes a shuttle and a drive motor in the control compartment connected to the shuttle wherein the shuttle is displaceable in a back and forth direction on actuation of the drive motor and wherein the shuttle is connected to a guide channel and a mechanism for raising and lowering the guide channel on back and forth displacement of the shuttle.

8. The tube handling system of claim 5 wherein the transport mechanism is an X-Y transport system with a support carriage that is transported in a back and forth first direction wherein the carrier of the push-pin is carried on the support carriage and is transported in a back and forth second direction orthogonal to the first direction.

9. The tube handling system of claim 1 wherein the housing has a base and the drive system includes a first drive motor with first drive belt that tracks around a drive wheel on the first drive motor and an idler wheel on the base wherein the drive belt is attached to the support carriage, and a second drive motor with a second drive belt that tracks around a drive wheel on the second drive motor, and around a first idler wheel on the base, around a second idler wheel on the support carriage, around a third idler wheel on a distal end of the support carriage and around a fourth idler wheel on the support carriage adjacent the second idler wheel, wherein the belt is attached to the push-pin carrier.

10. The tube handling system of claim 1 including a general purpose computer wherein the semi-automatic lab tube selection apparatus communicates with the general purpose computer and the general purpose computer provides a user interface for input of instructions to the control system of the tube selection unit.

11. A tube handling system with a semi-automatic lab tube selection apparatus for enabling a user to pick a select lab tube in a standard lab tube holding rack with open-bottom wells that contain one or more lab tubes comprising:
 a housing with a top deck having rectangular openings with tube rack supports and with a control compartment under the top deck,
 a tube selection module wherein at least one tube rack support on the top deck supports at least one tube holding rack on the tube rack support over at least one of the rectangular openings, the tube selection module having:
  a transport mechanism contained within the control compartment of the housing having a carriage assembly, wherein the carriage assembly has a carrier with a push-pin, a drive system that moves the carrier and the push-pin under the tube rack support, and an actuator that raises the push-pin on command, and
  a control system in the control compartment having electronic control components that operate the drive system to locate the carrier and the push-pin at a select location corresponding to a selected position under an open-bottom well of a tube rack positioned on the tube rack support, and that actuate the actuator to raise the push-pin, wherein a selected tube in the well of the tube rack at the selected position of the push-pin is raised for removal, and,
 a tube scanner module having:
  a glass scanner plate over one of the rectangular openings on the top deck wherein one of the tube rack supports on the top deck seats a tube holding rack over the glass scanner plate for scanning the open-bottom wells of the tube holding rack when supported by the tube rack support, and,
  a control system in the control compartment that operates in conjunction with the control system of the tube selection module to scan and identify tubes in a tube holding rack when located in the tube rack support of the tube scanner module.

12. The tube handling system of claim 11 in combination with a general purpose computer that is in communication with the control systems of the tube selection module and the tube scanner module.

13. The tube handling system of claim 11 wherein the tube supports of the tube selection module include a screen covering the rectangular openings, the screen having holes that align with the locations of tubes in a tube holding rack when the tube holding rack is located in the tube rack support.

14. The tube handling system of claim 13 wherein the holes are circular and sized to permit the push-pin to rise through a select hole and push a selected tube upwardly for convenient removal by a user.

* * * * *